(12) United States Patent
Lazevski et al.

(10) Patent No.: US 9,914,121 B2
(45) Date of Patent: Mar. 13, 2018

(54) TUBE FOR CHEMICAL, BIOLOGICAL OR BIOTECHNOLOGY MATTER, TUBE ARRANGEMENT, CARRIER FOR USE IN A TUBE ARRANGEMENT, USE OF A TUBE, AND METHOD FOR FORMING A TUBE

(71) Applicant: QIAGEN GMBH, Hilden (DE)

(72) Inventors: Sasa Lazevski, Hilden (DE); Thomas Voit, Hilden (DE)

(73) Assignee: QIAGEN GMBH, Hilden (DE)

( * ) Notice: Subject to any disclaimer, the term of this patent is extended or adjusted under 35 U.S.C. 154(b) by 0 days.

(21) Appl. No.: 14/769,932

(22) PCT Filed: Mar. 6, 2014

(86) PCT No.: PCT/EP2014/054302
§ 371 (c)(1),
(2) Date: Aug. 24, 2015

(87) PCT Pub. No.: WO2014/135613
PCT Pub. Date: Sep. 12, 2014

(65) Prior Publication Data
US 2016/0001288 A1      Jan. 7, 2016

(30) Foreign Application Priority Data
Mar. 6, 2013   (EP) .................................... 13158035

(51) Int. Cl.
| | | |
|---|---|---|
| *B01L 3/14* | (2006.01) |
| *B01L 3/00* | (2006.01) |
| *B01L 9/06* | (2006.01) |
| *G01N 35/04* | (2006.01) |

(52) U.S. Cl.
CPC ......... *B01L 3/5082* (2013.01); *B01L 3/50825* (2013.01); *B01L 9/06* (2013.01); *B01L 3/50* (2013.01); *B01L 2200/025* (2013.01); *B01L 2200/028* (2013.01); *B01L 2300/042* (2013.01); *B01L 2300/043* (2013.01); *B01L 2300/046* (2013.01); *B01L 2300/0609* (2013.01); *B01L 2300/0832* (2013.01); *G01N 2035/0491* (2013.01)

(58) Field of Classification Search
CPC ....................... B01L 2300/0609; B01L 3/5453
USPC ................................................. 422/550, 549
See application file for complete search history.

(56) References Cited

U.S. PATENT DOCUMENTS

| | | | |
|---|---|---|---|
| 4,895,650 A | | 1/1990 | Wang |
| 5,720,406 A | * | 2/1998 | Fassbind ............. B01L 3/50851 220/23.4 |
| 5,795,784 A | | 8/1998 | Arnquist et al. |
| (Continued) | | | |

FOREIGN PATENT DOCUMENTS

| | | |
|---|---|---|
| WO | 2012/056116 A1 | 5/2012 |
| WO | 2012122301 A2 | 9/2012 |

OTHER PUBLICATIONS

International Search Report From Corresponding PCT/EP2014/054302, dated May 8, 2014.

*Primary Examiner* — Natalia Levkovich
(74) *Attorney, Agent, or Firm* — McBee Moore Woodward & Vanik IP, LLC; Susan McBee

(57) ABSTRACT

A tube for chemical, biological or biotechnological matter is provided, wherein the tube has a positioning element, the positioning element shaped for engagement in a corresponding structure provided in a carrier.

7 Claims, 3 Drawing Sheets

(56) References Cited

U.S. PATENT DOCUMENTS

2010/0031760 A1 2/2010 Sherman et al.
2012/0328490 A1 12/2012 Loehn

* cited by examiner

TUBE FOR CHEMICAL, BIOLOGICAL OR BIOTECHNOLOGY MATTER, TUBE ARRANGEMENT, CARRIER FOR USE IN A TUBE ARRANGEMENT, USE OF A TUBE, AND METHOD FOR FORMING A TUBE

CROSS REFERENCE TO RELATED APPLICATIONS

This application is a § 371 National Stage Application of PCT/EP2014/054302, filed 6 Mar. 2014, which claims priority to EP 13158035.9, filed 6 Mar. 2013.

BACKGROUND

Field of the Invention

The invention pertains to a tube used in the field of chemical, biological and biotechnological processes. Especially, the invention relates to a tube which can contain fluid for in vitro amplification reaction, PCR and/or genotyping.

Description of Related Art

In vitro amplification procedures can be carried out in a small reaction tube which can be positioned within a thermal cycler or another laboratory device. The thermal cycler heats and cools the PCR tubes to achieve the specific temperatures required, especially the specific temperatures required for the polymerase chain reaction. The thermal cycler can provide a rotor or block for handling reaction vessels such as the tubes, especially for rotating the tubes (rotor) and/or heating and cooling.

For detecting the temperature and/or the amount of a specific substance in the tube optical measurements are carried out. The optical measurements determine an optical property of the fluid in the tube, for example a fluorescence signal. Thus, the tube can be irradiated with a light beam and a signal caused by the irradiation with light can be detected. An example for such a measurement is the QIAsymphony RGQ system of QIAGEN, Germany (www.qiagen.com).

WO 2012/006668 A1 discloses a multi vessel ring which comprises a ring body and a plurality of elongate tubes, each elongate tube being integrally formed with a ring body, and being pivotally connected to the ring body between an initial position in which a longitudinal access of each tube is generally parallel with an axis of rotation of the ring body, and a final position in which the longitudinal access of each tube is inclined relative to the axis of rotation of the ring body.

SUMMARY

It has been found that the use of tubes in practice causes difficulties because the alignment of the tube in the light beam used for optical measurement is not ideal and differs from tube to tube.

It is an object of the invention to provide for a tube which overcomes the difficulties of alignment of the tube with regard to the optical light beam used for investigation of the content of the tube.

The object is solved by the subject-matter of the independent claims.

By providing a tube according to the invention, deviating measurement results as a consequence merely of different positioning can be avoided, and it is possible to position each tube under the same conditions in the optical light beam. The tube alignment can be defined by a corresponding structure on/in a carrier. This corresponding structure can have a structure corresponding to the positioning element of the tube. Further, by providing single manufactured tubes the temperatures in each tube arranged in a thermal cycler can be considered to be the same in all tubes.

The tube can be a disposable tube and can be produced by injection moulding from a plastic material suitable for in vitro amplification processes. Preferably, the tube has a volume in the interval 0.1 to 2.0 ml, especially preferably 0.2 to 0.6 ml.

The term "positioning element" encompasses any geometry which can serve as a reference point for positioning and/or alignment of the tube in a carrier and/or a rotor of a thermal cycler. The positioning element can be formed as a pin, hook, nut, cavity, capping piece or the like.

The term "chemical, biological or biotechnological matter" encompasses especially blood, DNA, RNA, nucleic acids, oligonucleotides and/or aptamers.

DETAILED DESCRIPTION OF A PREFERRED EMBODIMENT

Figure 1:
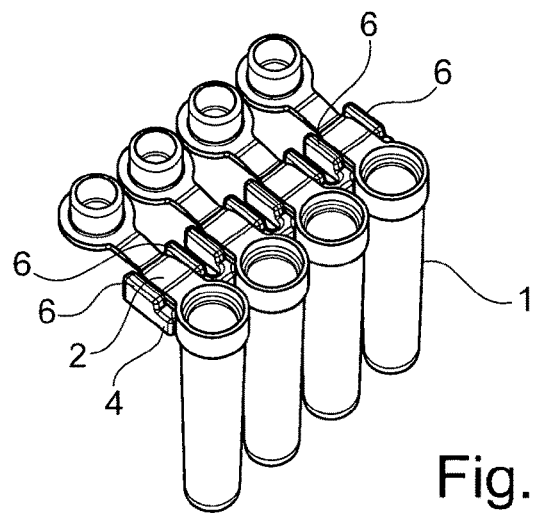
FIGS. 1-7 depict embodiments of disclosure described herein.

In a preferred embodiment, the tube can be integrally formed with the positioning element reducing the number of steps necessary for the manufacturing of the tube. Further, by providing the tube in a single piece with a positioning element the manufacturing process is simple because no specific alignment for forming the positioning element on the tube is necessary. Further, where the tube comprises a cap, the positioning element can be integrally formed with a cap of the tube. As an alternative, the positioning element can be located as a separate piece on the tube, for example as a collar.

In a preferred embodiment the positioning element of the tube and/or the corresponding structure of the carrier allows for pivoting of the tube. Thus, the positioning element allows for positing the tube in a carrier as well as for pivoting of the tube which reduces the number of elements necessary for handling the tube. In a preferred embodiment, the positioning element is formed as a pivot element which can define a pivot axis for pivoting the tube. Thus, the pivot element can serve as an element for pivoting the tube. Especially, the joint element can be a joint head pivot-mounted in a joint socket of a carrier.

Preferably, the positioning element comprises a projection extending parallel to the longitudinal direction of the tube body, preferably parallel to the elongate part of the tube. In a preferred embodiment the projection is formed on a bar, the bar extending transverse to the opening of the tube.

In a preferred embodiment, a carrier can be provided, in which more than 3 tubes, especially 4 tubes in a straight alignment or 72 tubes in a ring-shaped alignment can be positioned. Further, the tubes can be in a 96 well plate arrangement. Preferably, the carrier has a circumferential open receptacle for receiving a tube in case that the carrier provides for a straight alignment of tubes. Preferably, the carrier has a circumferential closed receptacle for receiving a tube in case that the carrier provides for a ring-shaped alignment. The carrier can have positioning elements for engagement with respective positioning elements of the tubes. The material used for manufacturing the carrier can be the same as the material used for the tube, however, a material, preferably a plastic, can be chosen which fulfils the requirements with regard to low-cost and mechanical demand.

The term "carrier" encompasses every structure which allows for positioning of more than 3 tubes in such that the tubes and the carrier can be handled as a unit, especially the carrier can be formed as an adapter. Thus, grabbing the carrier leads to the possibility to handle and/or move or carry the tubes positioned in the carrier. The carrier can be positioned for example in a rotor or similar device of a thermal cycler. The device of the thermal cycler is a known device comprising a plurality of openings each for accommodating one tube. The carrier as an adapter is adapted to the openings of the device. The geometric structure of the carrier can be adapted to the geometric structure of the device. The carrier can be an additional element to the device which can accommodate the tubes in the thermal cycler.

In a preferred embodiment a tube arrangement is provided, or in more than 3 tubes are positioned in a carrier, the carrier being non-unitarily form with the tubes. This tube arrangement allows for the positioning of tubes in a thermal cycler, each tube having the same optical properties with regard to the optical light beam used for investigation of the fluidic sample contained in the tube.

Other objects, features, advantages and aspects of the present application will become parent to those skilled in the art from the following description and dependent claims. It should be understood, however, that the following description, dependent claims and specific examples, while indicating preferred embodiments of the application, are given by a way of illustration only. Various changes and modifications within the spirit and scope of the disclosed invention will become really apparent to those skilled in the art reading the following.

Figure 2:
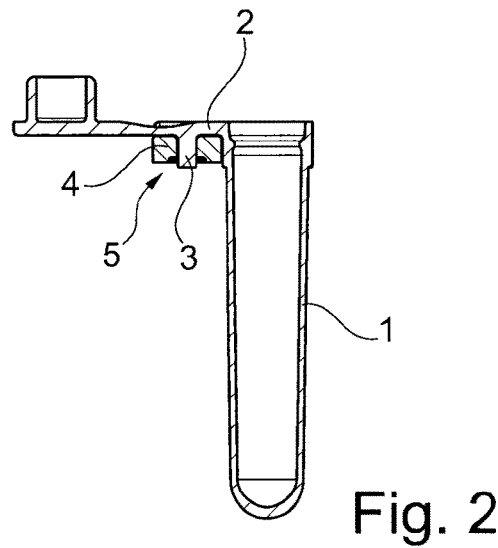
Figure 3:
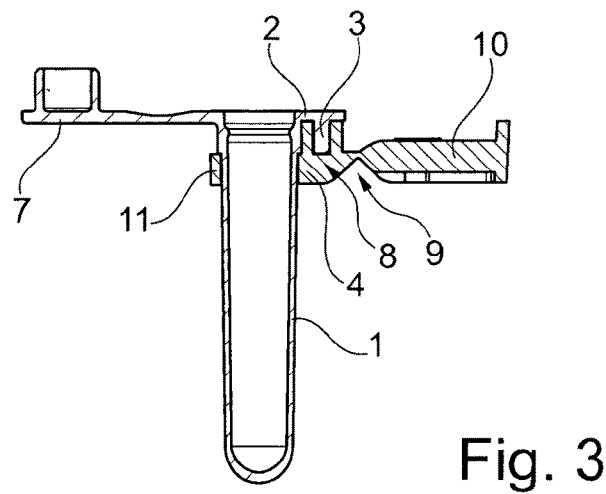
Figure 4:
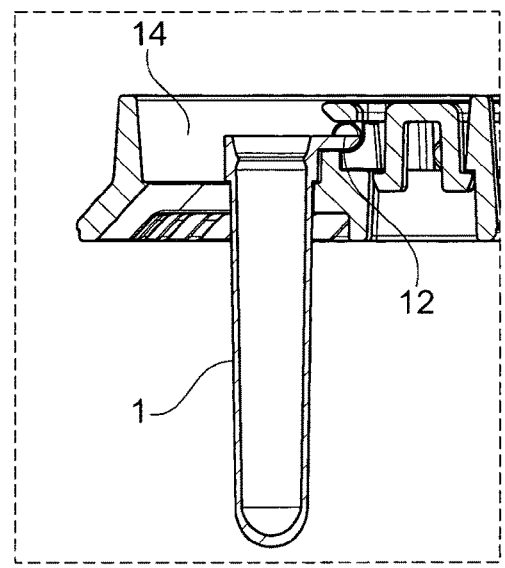
Figure 5:
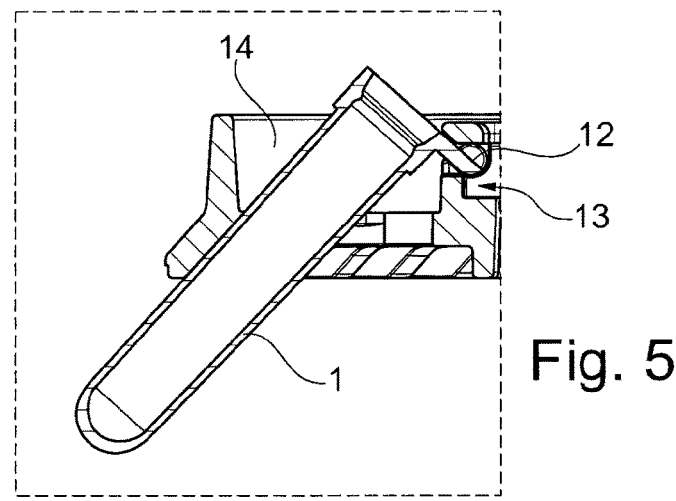
Figure 6:
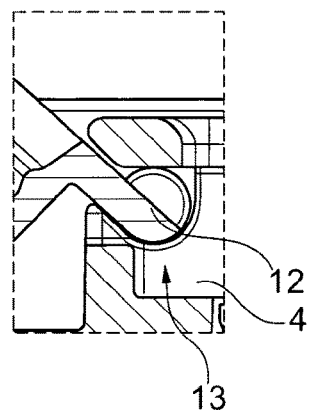

Examples of the invention will now be described with references to the accompanying drawings in which:

FIG. 1 schematically shows four tubes positioned in a carrier in a perspective view;

FIG. 2 is a sectional view of FIG. 1;

FIG. 3 schematically shows a tube positioned in a carrier in a sectional view;

FIG. 4 schematically shows a tube positioned in a carrier supported by a rotor;

FIG. 5 shows the tube positioned in the rotor according to FIG. 4 after pivoting the tube;

FIG. 6 shows an enlarged view of FIG. 5; and

Figure 7:
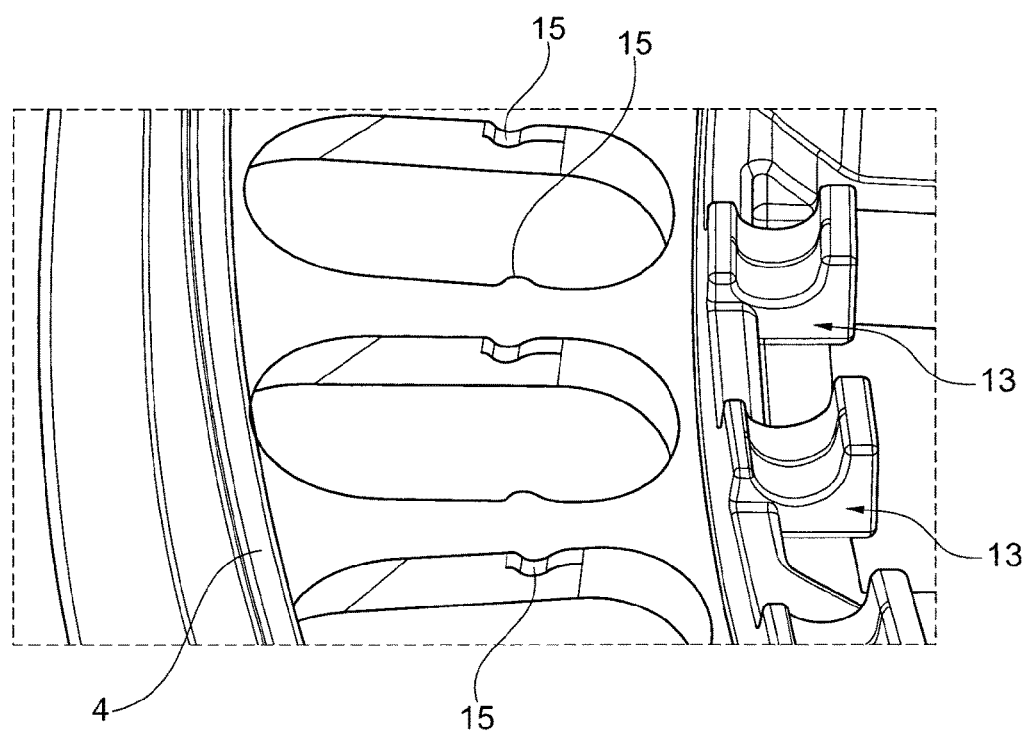

FIG. 7 shows the carrier according to FIGS. 4 and 5 in an enlarged view.

FIG. 1 shows four tubes 1. The each tube 1 has an open end and a closed end. Each tube 1 has an elongate body in which fluid can be filled. At the open end a bar 2 extends transverse to the open end of the tube 1. As can be further seen in FIG. 2, a projection 3 extends parallel to the longitudinal direction of the elongate tube body. The projection 3 is a positioning element for positioning the tube 1 in a carrier 4.

In the carrier 4 shown in FIG. 1 the tubes 1 are in straight alignment. The carrier 4 comprises openings 5. Each opening 5 is adapted and positioned to receive a projection 3. The openings 5 are positioning elements for engagement with a projection 3 of the tubes 1.

Further, the carrier 4 comprises side walls 6. The distance between two adjacent side walls 6 corresponds to the width of a bar 2. Due to the side walls 6 a further or alternative positioning of the tubes 1 with regard to the carrier 4 can be provided.

The tubes 1 shown in FIG. 1 further comprise each a closure or cap 7. In the embodiment shown in FIG. 1 the tube 1, bar 2, projection 3 and cap 7 are integrally formed. The carrier 4 is non-unitarily formed but manufactured in a different step than the tube 1. The tube 1 is positioned in a carrier 4 by alignment of the projection 3 in the opening 5 and/or the bar 2 between two side walls 6.

FIG. 3 schematically shows a tube 1 with a projection 3 as a positioning element positioned in a carrier 4. A blind hole 8 is formed in the carrier 4 for receiving the projection 3. The carrier 4 comprises a joint 9 for pivoting the tube 1 with regard to the carrier 4. In the embodiment shown in FIG. 3 the joint 9 is provided as an integral hinge. A section 10 spaced apart from a section 11 of the carrier 4 which receives the tube 1 can be mounted or fixed on a rotor of a thermal cycler.

In FIGS. 4 and 5 a tube 1 according to the invention is positioned in a carrier 4 by a positioning element which is used as a pivot element 12. The carrier 4 is positioned in a rotor 14 of a thermal cycler. In FIG. 4 the tube 1 is shown in its initial position. In FIG. 5 the tube is shown in its pivoted position with regard to the rotor 14. Whereas in FIG. 3 it is shown that the carrier 4 comprises a joint for pivoting the tube 1, in the embodiment shown in FIGS. 4 to 7 pivoting of the tube 1 is obtained by a movement of an element with regard to the carrier 4 to move or push the tube 1 from the position shown in FIG. 4 into the pivoted position shown in FIG. 5.

The pivot element 12 is integrally formed with the tube 1. The pivot element 12 is formed as a joint head which is positioned in a joint socket 13 of the carrier 4. The tube 1 is held in the pivoted position shown in FIG. 5 by a undercut 15 formed in the carrier 4 (see FIG. 7).

The invention claimed is:

1. Tube arrangement comprising a tube for chemical, biological or biotechnological matter and a carrier,
    wherein the tube has a positioning element, the positioning element shaped for engagement in an opening provided in the carrier,
    wherein the tube has an open end and a closed end,
    wherein the positioning element comprises a projection formed on a bar, the bar extending transverse to the open end of the tube,
    wherein the opening of the carrier is adapted to receive the projection,
    wherein the projection is external to the tube and extends parallel to the central axis of the tube from the bar, and
    wherein the projection extends from the bar to the closed end of the tube.

2. Tube arrangement according to claim 1, wherein the carrier is adapted to be mounted on a rotor of a thermal cycler.

3. Tube arrangement according to claim 1, further comprising a plurality of tubes, wherein the carrier is formed to position the plurality of tubes in a straight alignment or a ring-shaped alignment.

4. Tube arrangement according to claim 1, wherein the positioning element is formed as an integral part of the tube.

5. Tube arrangement according to claim 1, wherein the positioning element is formed as an integral part of a cap.

6. Tube arrangement according to claim 1, wherein the positioning element is provided separately from the tube.

7. Method for performing an in vitro amplification measurement, comprising using the tube arrangement according to claim 2 and positioning the tube arrangement in the rotor of the thermal cycler.

* * * * *